(12) United States Patent
Steffan

(10) Patent No.: US 8,969,596 B2
(45) Date of Patent: Mar. 3, 2015

(54) SYNTHESIS OF EQUOL

(76) Inventor: Bert Steffan, Köln (DE)

( * ) Notice: Subject to any disclaimer, the term of this patent is extended or adjusted under 35 U.S.C. 154(b) by 903 days.

(21) Appl. No.: 13/058,558

(22) PCT Filed: Aug. 12, 2009
(Under 37 CFR 1.47)

(86) PCT No.: PCT/EP2009/060450
§ 371 (c)(1),
(2), (4) Date: Oct. 7, 2011

(87) PCT Pub. No.: WO2010/018199
PCT Pub. Date: Feb. 18, 2010

(65) Prior Publication Data
US 2012/0094336 A1    Apr. 19, 2012

Related U.S. Application Data

(60) Provisional application No. 61/088,843, filed on Aug. 14, 2008.

(30) Foreign Application Priority Data

Aug. 14, 2008   (EP) ..................... 08162407

(51) Int. Cl.
C07D 311/74    (2006.01)
C07D 311/34    (2006.01)
C07D 311/38    (2006.01)

(52) U.S. Cl.
CPC ............ *C07D 311/34* (2013.01); *C07D 311/38* (2013.01)
USPC ....................................... 549/403

(58) Field of Classification Search
CPC ................................................ C07D 311/74
See application file for complete search history.

(56) References Cited

U.S. PATENT DOCUMENTS 8,263,790 B2 *   9/2012   Setchell et al. ............... 549/399

FOREIGN PATENT DOCUMENTS

WO    WO2007/016423 A2    2/2007
WO    WO 2010018199 A1 *  2/2010

OTHER PUBLICATIONS

Joannou et al. 1995. A Urinary Profile Study of Dietary Phytoestrogens. The Identification and Mode of Metabolism of New Isoflavonoids. Journal of Steroid Biochemistry and. Molecular Biology, vol. 54, No. 3/4, pp. 167-184.*
Rofer et al. 2006. Structural Elucidation of Hydroxy-Lated Metabolites of the Isoflavan Equol by Gas Chromatography-Mass Spectrometry and Highperformance Liquid Chromatography-Mass Spectrometry. Drug Metabolism and Disposition, vol. 34, No. 1, pp. 51-60.*
Goto, H., et al. "Synthesis of Various Kinds of Isoflavones, Isoflavanes, and Biphenyl-Ketones, and Their 1,1-Diphenyl-2-picrylhydrazyl Radical Scavenging Activities." Chem. Pharm. Bull. (2009). vol. 57 (4), pp. 346-360.*
Gharpure et al., "o-Quinone methide based approach to isoflavans: application to the total syntheses of equol, 3'-hydroxyequol and vestitol," Tetrahedron Letters, vol. 49, pp. 2974-2978 (2008).
Heemstra et al., "Total Synthesis of (S)-Equol," Organic Letters, vol. 8, No. 24, pp. 5441-5443 (2006).
Muthyala et al., "Equol, a natural estrogenic metabolite from soy isoflavones: convenient preparation and resolution of R- and S-equols and their differing binding and biological activity through estrogen receptors alpha and beta," Bioorganic & Medicinal Chemistry, vol. 12, pp. 1559-1567 (2004).
Thakar et al., "Reductions with Diborane & Sodium Borohydride in the Presence of Lewis Acids: Part II-Benzopyrones," Indian J. of Chemistry, pp. 74-77 (1965).

* cited by examiner

*Primary Examiner* — Noble Jarrell
*Assistant Examiner* — John S Kenyon
(74) *Attorney, Agent, or Firm* — Sonapat LLC

(57)   ABSTRACT

Subject of the invention is a method for the production of isoflavanes from isoflavones, whereby in a first reaction step (a) the 4-keto group of the isoflavone is reduced in a enantioselective manner, whilst the 2,3-double bond is maintained, to the 4-hydroxy compound.

13 Claims, 2 Drawing Sheets

S-Equol

SYNTHESIS OF EQUOL

This is the U.S. national stage entry of International Application No. PCT/EP2009/060450, filed on Aug. 12, 2009, which claims priority to U.S. Provisional Application No. 61/088,843, filed on Aug. 14, 2008, and which also claims priority to European Application No. 08162407.4, filed on Aug. 14, 2008.

BACKGROUND OF THE INVENTION

The subject of the invention is a method for the production of isoflavanes from isoflavones.

Isoflavones, also referred to as isoflavonoids, are compounds of mostly yellow coloration, which are derivatives of isoflavones and thus flavonoids. Isoflavones are secondary compounds from plants, which, amongst others, play a role in the plants' defense from pathogens. The ground body of isoflavone is found in clover species. Some well-known isoflavones are daidzein, found as a glucoside of daidzin in soy flour, genistein from soy beans and red clover, prunetin from the bark of plum trees, biochanin A from chickpeas and clover, orobol, santal from sandle wood, red wood and other woods and pratensein from fresh red clover.

The isoflavone Daidzein [4',7-dihydroxyisoflavone; 7-hydroxy-3-(4-hydroxyphenyl)-4H-1-benzopyran-4-one] is found in soy and is thus part of many foods and dietary supplements. The isoflavane equol [4',7-dihydroxyisoflavane; 3-(4-hydroxyphenyl)-7-chromanol] is produced in the intestinal flora after consumption of daidzein. Equol is thus part of the group of secondary plant metabolites. It is assumed that the conversion is carried out by streptococci, lactamid acid bacteria and bifido bacteria. After the consumption of foods which are rich in daidzein, equol is detectable in blood and urine. Equol has a mild estrogenic activity (0.1% of the activity of steroid-estrogens) and can bind to the estrogen receptors ERα and ERβ. Only about a third (Caucasian population) up to half (Japanese population) of humans can produce equol from daidzein. In humans who are capable of producing equol ("equol producers"), the cholesterol reducing and anti-inflammatory effect of a soy-rich diet is more pronounced compared to humans, which are not capable of producing equol. Especially for S-equal, various anti-proliferative influences were shown and documented in studies, for instance, with respect to tissue changes in the breast, which may occur in females during the menopause. Equol also inhibits DHT production in males due to interactions with the 5α reductase. It is assumed that DGT is a cause in the forming of prostate cancer in males. Since equol is produced only in the intestine from daidzein, it can not be isolated from natural products and has to be produced artificially. Various publications disclose ways of production by microbiological methods. In this respect, EP 1025850 discloses a composition in which equol is produced microbiologically from isoflavones from soy. Microbiological production processes are disadvantageous in many respects. For instance, they are prone to disturbances, because microorganisms may change and thus yield different products. The product process thus has to be continually supervised. Frequently, the microorganisms have to be killed and removed from the composition after the production is completed.

Thus, it was tried to produce equol by means of organic synthesis.

Muthyala et al., 2004, describe a method for the production of equol from daidzein. The method comprises a reduction of the 2,3-double bond and the keto group in the presence of a palladiumhydroxide-catalyst of the formula $Pd(OH)_2$. A racemate is obtained, which is subsequently separated into R-equol and S-equol by means of chromatography (HPLC).

Heemstra et al., 2006, disclose an asymmetric synthesis of the chromane-ring by means of Evans-alkylation and intra molecular etherification according to Buchwald.

The WO 2007/016423 A2 discloses a method for the reduction of the 2,3-double bond and the 4-keto group, elimination of 4-OH-group under formation of a 3,4-double bond, synthesis of a specifically applicable iridium-catalyst and subsequent enantioselective reduction of the 3,4-double bond with the iridium catalyst.

Gharpure et al., 2008, disclose a method for the total synthesis of various isoflavanes and equol.

Methods for the reduction of benzopyranes with boron hydrides and diboranes are disclosed in Thakar et al., Indian J. of Chem., 1965, 74-77.

The advantageous effects of isoflavones and phytoestrogens such as equol are usually observed, if the compounds are consumed over an extended time period in significant amounts. Since the equol precursor daidzein is found in comparatively large amounts in soy, equol could be administered as a dietary supplement (food supplement, nutritional supplement). It would thus be highly desirable that equol is available by a simple production method, in large amounts and at low costs.

The known methods of organic synthesis have the disadvantage that they are relatively complicated and require special and costly reagents. A simple and cost-efficient production which could be the basis for supplying large parts of the population with a daily dosis, is not possible with these methods. The known methods are not appropriate for cost-efficient industrial production, because they require either expensive catalysts comprising precious metals or specific chiral compounds, which are difficult to synthesize, as catalysts or protective groups. Moreover, the known methods generally require a separation of enantiomers from a racemate, which significantly increases the workload and thus the costs of industrial production.

The Problem Underlying the Invention

The problem underlying the present invention is the provision of a method for the simple and cost-efficient production of isoflavanes, especially of equol. The method shall be carried out in as few reaction steps as possible. The use of chemicals which are expensive and have to be manufactured in a complicated manner, especially of precious metals such as platinum and of special reagents, such as complex chiral iridium catalysts, shall be avoided. The method shall allow the synthesis of different isoflavanes and derivatives of equol in a simple manner.

THE SUBJECT OF THE INVENTION

The problem underlying the invention is surprisingly solved by methods and compounds with the features of claims 1 to 9.

FIG. 1 schematically shows the reaction of daidzein to S-equol.

Figure 1:
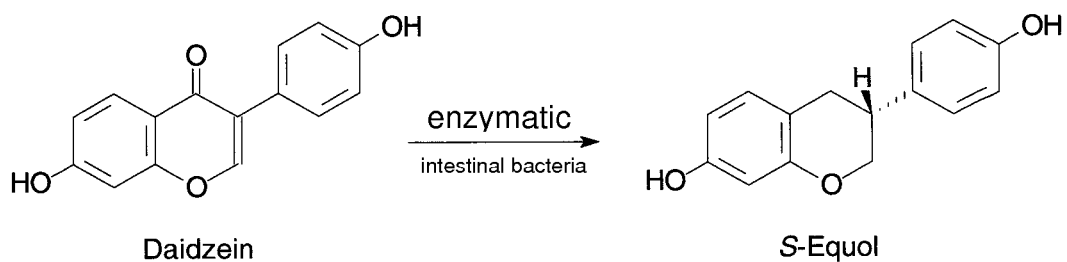
Figure 2:
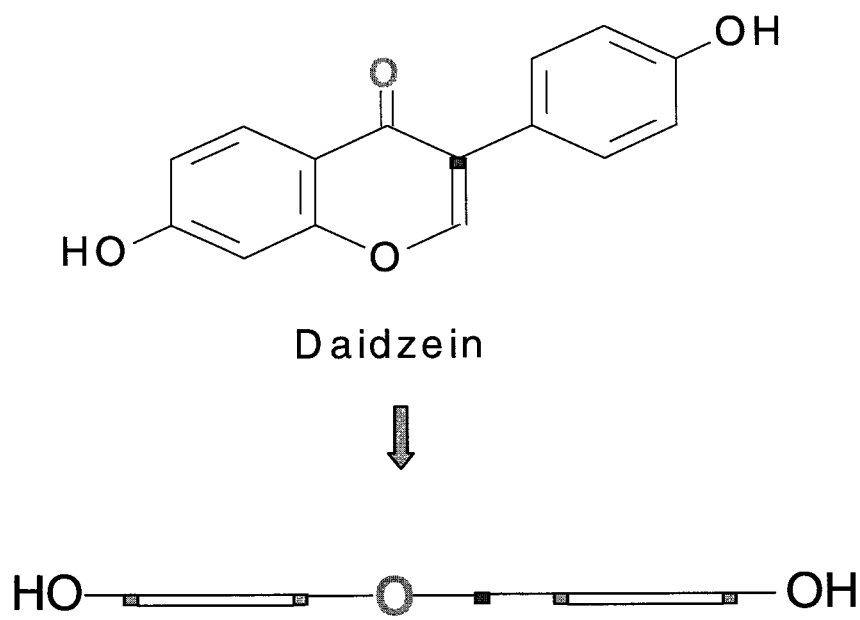
FIG. 2 shows the starting compound daidzein as a structural formula (above) and tilted by 90° (below). From this perspective, the 4-CO-group points towards the viewer.
Figure 3:
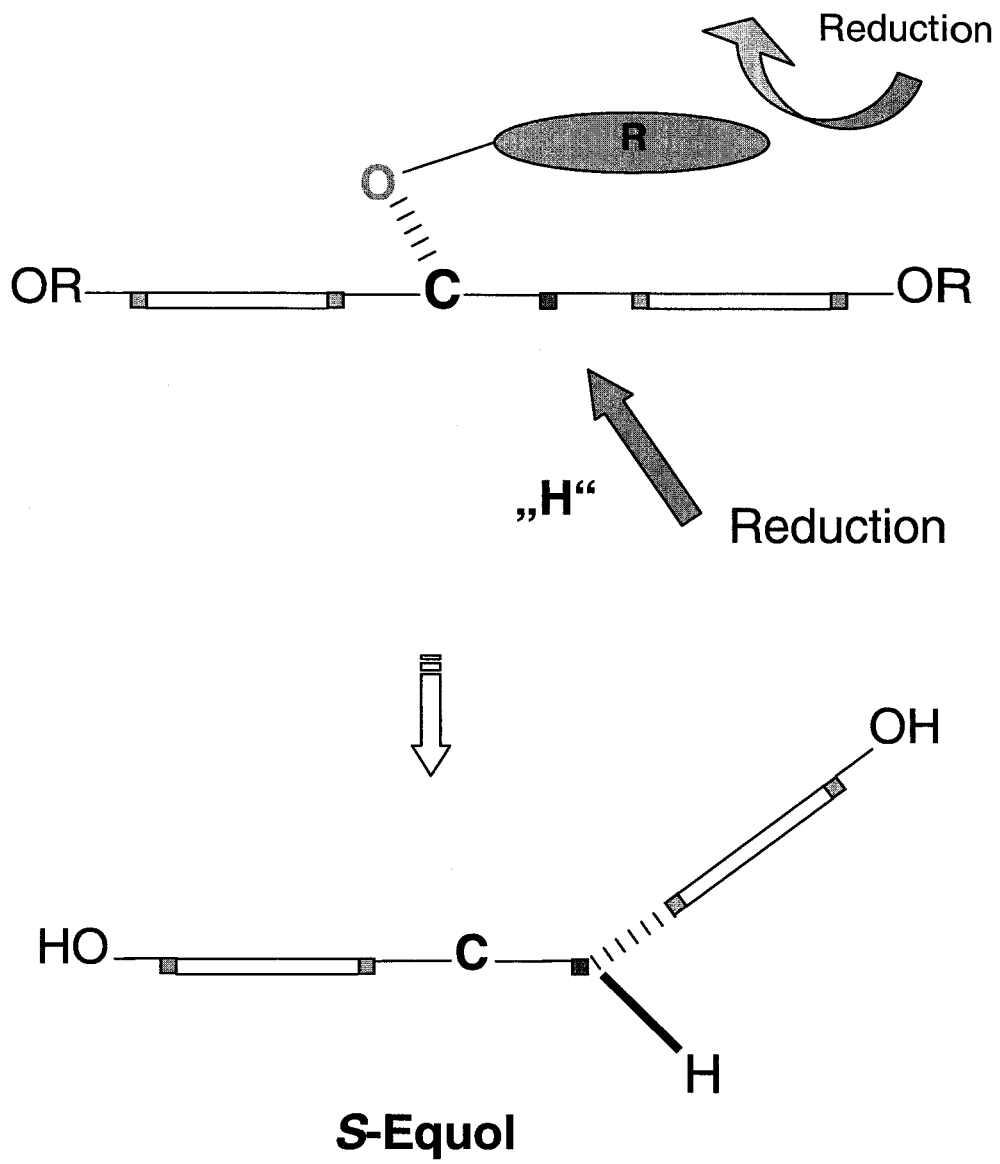
FIG. 3 shows a side view of reduced daidzein with a protective group at the 4'-position. The 4-RO-protective group blocks the upper side of the molecule and allows the reduction exclusively from the bottom side.

The inventive method is based on the following consideration: By selectively blocking the upper or lower side of the isoflavone, which is selectively hydrogenated at the 4-position, whereby the blocking is preferably mediated by etherification or esterification of the 4-hydroxy group, the cis-attack of a reducing agent for the reduction of the 2,3-double bond is sterically directed. As shown in FIG. 3, the attack of the reducing agent occurs either at the upper or lower side, depending on the position of the 4-RO-group. The reaction can thus be carried in a simple manner and by using comparatively simple and inexpensive catalysts and reducing agents.

In the method of the invention for the production of isoflavanes from isoflavones, in a first reaction step (a) the 4-keto group of the isoflavone is reduced in an enantioselective manner to the 4-hydroxy compound, whilst maintaining the 2,3-double bond. The hydroxy compound thus obtained is 3-(4-hydroxyphenyl-)-4,7-dihydroxy-chromene-2. Depending on the choice of the reaction conditions, the chiral compound 3-(4-hydroxyphenyl-)-4(S)-hydroxy-,7-hydroxy-chromene-2 or 3-(4-hydroxyphenyl-)-4(R)-hydroxy-,7-hydroxy-chromene-2 is obtained. The chiral carbon atom of the 4-hydroxy compound is the one at the 4-position. As a reaction product, the 4R- or 4S-form of the 4-hydroxy derivative of the starting compound is obtained. The reaction occurs selectively at the 4-position of the molecule. The rest of the molecule remains essentially unchanged. By the first reaction step (a), a chiral intermediate product is obtained already in an early stage of the synthesis. During further conversion of the initial immediate product to the isoflavane, the chirality of the molecule is maintained. Thus, a separation step, in which a racemate has to be separated into the two enantiomers, is avoided. The reaction products from step (a) can thus be converted to the chiral 3S- or 3R-isoflavane with a chiral 3C-atom in subsequent reaction steps. The hydroxy compounds are thus essential inventive intermediate products for the further synthesis. They may be isolated and further processed as necessary.

The reduction (a) is carried out in the presence of an appropriate enantioselective reducing agent. Such compounds are known to one skilled in the art. Useful reducing agents are disclosed for instance in March's Advanced Organic Chemistry: Michael B. Smith, Jerry March 2007, publisher: Wiley. In preferred embodiments, the reduction is carried out enzymatically or with LiAlH(O-tert-Bu), 9-BBN or Alpine borane. 9-BBN is an abbreviation for 9-borabicyclo[3.3.1]nonane. Alpine borane stands for B-3-pinanyl-9-borabicyclo [3.3.1]nonane.

In the reduction step (a), a chiral product is obtained from a non-chiral educt. Thus the reduction is an assymetric synthesis. In order to obtain the chiral product, a chiral compound has to be present in the reduction step. According to the present invention, it is preferred that the chiral compound is an enantionselective reducing agent. However, the chiral compound may also be a chiral auxiliary agent, which is not the reducing agent.

In a preferred embodiment, the enantioselective reducing agent is an organoborane. Boron organic compounds are often used in assymetric synthesis due to their ability to form adducts with keto groups. Especially preferred is catechol borane. Assymetric reductions of allylic ketones to obtain allylic alcohols in the presence of catechol borane are disclosed by Corey et al., 1987, 1990 and 1998.

In preferred embodiments, the reduction step (a) is an assymetric addition of an organozinc-reagent in the presence of chiral ligands. This reaction is described by Soai et al., 1992.

In another embodiment of the invention, the reduction step (a) includes an epoxidation according to Sharpless. Such a method for preparing chiral allylic alcohols from allylic ketones is disclosed by Johnson et al., 2000. However, this reaction has the drawback that the maximum yield is 50%.

In another embodiment of the invention, the reduction step (a) is carried out by palladium catalysed assymetric transformation (DYKAT). This reaction is described by Lüssem et al., 2003.

Preferably, the chiral 4S- or 4R-hydroxy compound obtained in step (a) is further processed in a second reaction step (b). The reaction step (b) may be carried out without further purification steps in the same reaction batch, optionally after neutralization and/or removal of remaining reactive components. Alternatively, it is also possible to purify the hydroxy compound before step (b).

In a preferred second reaction step (b), a protective group is attached to the enantiomeric 4-hydroxy compound. The 2,3-double bond is maintained. Preferably, the reaction (b) is an esterification or an etherification. The hydroxy group at the 4-position in the molecule thereby is converted selectively to an ether- or ester group. In reaction step (b), it occurs that protective groups are also attached to the further hydroxy groups in the molecule or at least to some of these further hydroxy groups. In a further embodiment of the invention, the reaction occurs selectively only at the 4-position.

Depending on the position of the 4-hydroxy group, the protective group blocks the upper or lower side of the molecule, such that the subsequent attack of a reducing agent in a reaction step (c) may occur exclusively, or essentially, from the other side which is not blocked (see FIG. 3). As the result of this enantioselective reduction, depending on the initial stereochemistry of the 4-RO group, either the (3R-) or (3S-) isoflavane is obtained as the product after removal of the protective group.

Preferably, the protective group is a bulky substituent. Frequently, bulky substituents comprise branched alkyl moieties or ring structures, wherein the ring structures comprise at least one aliphatic or aromatic ring. In preferred embodiments, the rings are benzyl, hexyl or norbornyl rings. Preferably, the branched alkyl moieties comprise at least 4, especially 4 to 30 or 6 to 20 carbon atoms. Protective groups for the attachment to hydroxy moieties, which may be used according to the invention, are generally known to the skilled person and may be chosen accordingly (see for instance Greene's Protective Groups in Organic Synthesis; Peter G. M. Wuts, Theodora Greene, publisher: Wiley, 2006). Useful protective groups are, for example, 2-methoxy-ethoxymethyl (MEM), benzyl, tert-butyl, toluoylsulfonyl and silyl, especially trimethylsilyl groups.

The reaction product resulting from step (b), which is the 4S- or 4R-hydroxy derivative of the educt protected at the 4-position, is preferably further reacted in a third reaction step (c), wherein the 2,3-double bond of the protected 4-hydroxy compound is reduced. During this reaction step, the protected 4-hydroxy group is also reduced. Naturally, the 4-protective group is removed thereby at the same time. An isoflavane is obtained. The product has a chiral C-atom at the 3-position. Depending on the choice of the starting compound and the reducing agent, it is thus possible to produce a 3S- or 3R-isoflavane.

The enantioselective reduction of the 2,3-double bond can be carried out by using simple, common and inexpensive catalysts. It is not necessary to use chiral catalysts in this reaction step. Rather, one side of the molecule is shielded by the protective group, such that the reducing agent can react selectively at the other side of the molecule. The hydrogenation of the double bond occurs thus in a cis-manner only on one side of the molecule (see FIG. 3). The reaction occurs selectively at the 2-, 3- and 4-position of the molecule. The protected 4-hydroxy group and the 2,3-double bond are not reduced to alkyl groups. Other portions of the molecule are not or essentially not reduced.

If further hydroxy groups in the molecule, for example at the 4'- and 7-position, were protected by protective groups, they can also be removed in reaction step (c). In case such additional protective groups should not be removed during reaction (c), they may be removed during subsequent reaction steps if desired or necessary. Such an additional cleavage of remaining protective groups may for instance be carried out with $LiAlH_4$ or according to other methods known in the art (see for instance Greene's Protective Groups in Organic Synthesis; Peter G. M. Wuts, Theodora Greene, 2006, publisher: Wiley).

In the reaction step (c), common reducing agents may be used which are capable of selectively reducing the double bond and the substituted 4-alcohol group. Such compounds are known in the art and are for instance disclosed in March's Advanced Organic Chemistry; Michael B. Smith, Jerry March, 2007, publisher: Wiley. In preferred embodiments of the invention, the reaction step (c) is carried out by hydroboration with subsequent protolytic reaction, by addition of diamides, by reduction with BINAP, Wilkinson catalysts, Vaska catalysts, silanes or by enzymatic reduction, preferably with enoyl-ACP-reductase.

The hydroboration is a reaction commonly used in organic chemistry. In the hydroboration of alkenes with borane, an alkylborane is obtained. This intermediate product is converted to the alkane by a protolytic reaction carried out in situ. For example, the hydroboration may be carried out with 9-BBN, and the protolytic reaction for example with a proton donator, such as formic acid or propionic acid.

A preferred diamide is hydrazine of the formula $N_2H_4$.

BINAP (2,2'-bis(diphenylphosphino)-1,1'-binaphthyl) is a bidentate diphospinic ligand with axial chirality, which displays extraordinary properties with respect to enantioselectivity and activity in many reactions catalyzed by transition metals, such as asymmetric hydrogenation. Wilkinson catalysts are homogeneous catalysts used in organic chemistry of the formula compound $C_{54}H_{45}ClP_3Rh$. These rhodium complexes are used in hydrogenation, hydroformulation, hydrosilylation and in the isomerisation of allyl groups to propenyl groups.

Vaska catalyst (Vaska complex) is the trivial name for the iridium compound trans-chlorocarbonylbis(triphenylphosphin)iridium(I). This quadratic-planar diamagnetic complex consists of a central iridium atom, to which two triphenylphosphinic ligands are attached in a trans-arrangement. Besides, a chloride and a carbonyl ligand are in the coordination sphere of the metal.

Silanes are reactive compounds, which comprise at least one Si—H or Si—R bond, wherein R is an organic moiety.

Enzymes, which selectively reduce double bonds, are known in the art. The enzyme enoyl-ACP-reductase catalyzes the reduction of crotonyl-ACP to butyryl-ACP by consumption of NADPH.

The isoflavane produced according to the invention may be purified in a step (d) after the course of the reaction (c). The purification may be carried out by employing known methods, such as distillation, recrystallization, chromatography and/or filtration. Such purification steps may also be carried out after the reaction steps (a) or (b). In preferred embodiments, the steps (a) and (b) or the steps (b) and (c) and especially all three steps (a) to (c) are carried out subsequently without intermediate purification steps of intermediate products. Thus, the entire reaction may be carried out within one batch.

The method of the invention may be carried out in only a few simple steps. In a preferred embodiment of the invention, the synthetic method consists of the reaction steps (a), (b) and (c). An additional enantiomeric separation step is not necessary. Preferably, the method does not comprise an additional step in which enantiomers are separated from each other.

Preferably, the final product of reaction step (c), as well as the intermediate product of the first reaction (a) or (b), comprises the S- or R-form in high purity. Preferably, the reaction product of step (a), (b) or (c) comprises at least 70, 85 or 90%, preferably at least 95, 98 or 99% of the desired R- or S-stereoisomer.

In the inventive process, it is not necessary to use precious metals, such as silver, gold, platinum or palladium. In a preferred embodiment, the entire method is carried out without the use of precious metals. The use of chiral heavy metal catalysts, such as iridium catalysts, is also not necessary. In a preferred embodiment, the entire process is carried out without using chiral heavy metal catalysts.

As a starting compound in the inventive method, it is preferred to use daidzein. As a natural isoflavone, daidzein is available in large amounts. For instance, daidzein may be used which was isolated from soy extracts or which is part of soy extracts. Therefore, the inventive method has the advantage that already the starting compound is inexpensive. When using daidzein as the starting compound, enantiomeric equol is obtained as the reaction product. In preferred embodiments of the invention, either the S-form or the R-form of equol is produced. For the S-form of equol, in summary more advantageous physiological influences are known.

However, according to the invention it is possible to use any known isoflavones as starting compounds. In a preferred embodiment, derivatives of daidzein are used as starting compounds. As a reaction product, instead of equol a corresponding derivative of equol is obtained. The term "derivative" as used herein applies to substances which have the structure of the stem compound (daidzein or equol) and comprise at least one additional substituent. Derivatives are especially also compounds, in which the hydroxy groups are not, or not exclusively, at the 4'- and 7-position, but at different or additional positions, for instance at the 5'- and 6'-position.

If a derivative of daidzein is used as the starting compound, the end product (the corresponding equol derivative) comprises the same substituents at corresponding positions of the structural formula. The substituent or the substituents are preferably selected in a manner that the reaction of the invention is not negatively affected or essentially not negatively affected by the constituents. This is generally not problematic, because common substituents such as hydroxy groups or alkyl moieties at both benzyl rings of the isoflavone do not negatively affect the reactivity of the 4-keto group and 2,3-double bond to a significant extent.

Useful derivatives of isoflavones/isoflavanes are for example those, in which the basic chemical formula has further substituents attached to one or both phenyl rings, for instance alkyl, aryl, araryl, alkoxy, halogen, hydroxy, nitro, sulfate, sulfonate, hydroxamate or imino moieties. These substituents may also be attached to the 2C-atom of daidzein. The alkyl substituents especially comprise 1 to 10 carbon atoms and are branched or linear, for instance methyl, ethyl, propyl, isopropyl or butyl groups. The alkyl, aryl, araryl and alkoxy substituents may be substituted with hetero-atoms, for instance with hydroxy, amine, alkoxy or halogen groups. Further useful derivatives of daidzein are compounds, in which one or more hydroxy groups are esterified or etherified, especially at the 4'- and/or 7-position. The derivatives may also comprise at least one hydroxy group attached to a position different from the 4'- or 7-position. Suitable derivatives are, for instance, daidzin, 3'-hydroxydaidzein for the synthesis of 3'-hydroxyequol, 2',3'-hydroxydaidzein for the synthesis of 2',3'-hydroxyequol and 4'-methoxy-2'-hydroxydaidzein for the synthesis of vestitol (4'-methoxy-2'-hydroxyequol).

In a further preferred embodiment of the invention, the reaction step (c) is carried out in a manner such that a derivative of the isoflavane, especially of equol, is obtained, which is substituted at the 2C-position. This is possible in a simple manner, if the hydroboration is not followed by a protolytic reaction, but by a different reaction. Thereby, for instance a hydroxy group or alkoxy group may be introduced at the 2C-position.

EXAMPLES

Example 1

Reduction of the 4-keto-function of Daidzein (1) to the 4-(R)-hydroxy Group

To a solution of (S)—CBS-oxazaborolidin (0.1 eq) in THF (tetrahydrofurane), a solution of N-ethyl-N-isopropylanilinborane (1 eq) in THF was added. To this mixture, a solution of daidzein (1 eq) dissolved in THF was added slowly and dropwise at 25° within 1.5 hours. Subsequently, the reaction mixture was stirred for additional 10 minutes, quenched carefully with methanol and stirred for 30 minutes. The solvent was removed in a rotary evaporator and the product was purified by flash chromatography on a silica gel (230-400 mesh) with the eluant ethyl acetate/hexane (4:1 v/v). The enantiomeric purity was determined by HPLC in a chiral column to 96% ee (25 cm Chiralcel OD-H chiral column; iso-PrOH/hexane: 1/99; flow rate: 0.3 ml/min; detection: 254 nm); the yield was 78% daidzein-4-ol (2).

Example 2

Protection of the 4,7,4'-hydroxy Groups of Dihydrodaidzein

Especially the 4-hydroxy group is protected with a bulky substituent in order to sterically block the R-side of the molecule. As a substituent, bromobenzylbromide is used. Besides the 4-hydroxy group, also the other two aromatic hydroxy groups are etherified. 3.5 eq NaH were stirred into water-free THF with 0.35 eq p-BrC6H4CH2Br and 0.1 eq dihydrodaidzein (2) obtained according to example 1 in THF under a backflow for 12 hours. After flash chromatography at a silica gel (230-400 mesh) with the eluant ethylacetate/hexane (4:1 v/v), the yield was 80% daidzein-4,7,4'-tri-bromobenzylether (3).

Example 3

Reduction of the 2,3-double Bond in Chromene System (3) with 9-BBN

To a solution of compound (3) (1 eq) in water-free THF, 1 eq 9-BBN was added dropwise at room temperature under stirring and nitrogen atmosphere. After stirring for 1 hour at room temperature, 2 n formic acid were added dropwise and further stirred for 1 hour at a maximum temperature of 30° to 40° C. The reaction mixture was diluted with ether and washed twice with water. The organic supernatant was evaporated by rotating and purified by flash chromatography at a silica-gel (230-400 mesh) with the eluants ethylacetate/hexane (4:1 v/v). The enantiomeric purity was determined by HPLC at a chiral column as 98% ee (25 cm Chiralcel OD-H chiral column; A ethanol/hexane: 10/90; B ethanol/hexane 90/10; gradient 15 min; flow rate: 1 ml/min; detection: 254 nm); yield 75%:2,3(S)-dihydrodaidzein 4,7,4'-tri-bromobenzylether (4).

Example 4

Removal of the Hydroxybenzyl Group

To a suspension of $LiAlH_4$ in ether, compound (4) dissolved in ether is added dropwise and stirred under backflow for about 3 hours. The reaction flask is cooled with ice water, and ice water is added carefully dropwise to the reaction mixture, until the development of hydrogen terminates. Subsequently, 10% sulphuric acid is added until the aluminium hydroxide precipitate is dissolved. The organic phase is removed in a reparatory funnel and purified by flash chromatography at a silica-gel (230-400 mesh) with the eluants ethylacetate/hexane (4:1 v/v). The enantiomeric purity of the product is determined by HPLC at a chiral acid as 98% ee (25 cm Chiralcel OD-H chiral column; A ethanol/hexane 10/90; B ethanol/hexane 90/10; gradient 15 min; flow rate: 1 ml/min; detection: 254 nm), yield: 95% (S)-equol.

LITERATURE

Muthyala, R. S., Ju, Y. H., Sheng, S., Williams, L. D., Doerge, D. R., Katzenellenbogen, B. S., Helferich, W. G. and Katzenellenbogen, J. A. (2004): "Equol, a natural estrogenic metabolite from soy isoflavones: convenient preparation and resolution of R- and S-equols and their differing binding and biological activity through estrogen receptors alpha and beta", Bioorg. Med. Chem., 12, 1559-1567.
Heemstra, J. M., Kerrigan, S. A., Doerge, D. R., Helferich, G. H., Boulanger, W. A. (2006): "Total Synthesis of (S)-Equol", Organic Letters, 8, 5441-5443.
Gharpure, S. J., Sathiyanarayanan, A. M., Jonnalagadda, P. (2008): "o-Quinone methide based approach to isoflavans: application of the total syntheses of equol, 3'-hydroxyequol and vestitol". Tetr. lett. 49, 2974-2978.
Soai, K.; Niwa, S. Chemical Reviews 1992, 92, 833-856.
Corey, E. J.; Bakshi, R. K.; Shibata, S. J. Am. Chem. Soc. 1987, 109, 5551-5553.
Corey, E. J.; Bakshi, R. K.; Shibata, S.; Chen, C.-P.; Singh, V. K. J. Am. Chem. Soc. 1987, 109, 7925-7926.
Corey, E. J. Pure Appl. Chem. 1990, 62, 1209-1216.
Corey, E. J.; Helal, C. J. Angew. Chem. 1998, 110, 2092-2118].
Johnson, R. A.; Sharpless, K. B. Catalytic Asymmetric Synthesis (Ed.: Iwao Ojima), Wiley-VCH, New York, 2000.
Lüssem, B. J.; Gais, H.-J. J. Am. Chem. Soc. 2003, 125, 6066-6067; Diss.: Asymmetrische Synthese von allylischen Alkoholen mittels Palladium-katalysierter asymmetrischer Transformation von allylischen Carbonaten"; Ralf Helmut Hetzer; Rheinisch-Westfälischen Technischen Hochschule Aachen 2008.

The invention claimed is:
1. A method, which comprises in a first reaction step (a) reducing the 4-keto group of an isoflavone in an enantioselective manner to produce a 4-hydroxy-compound, while the 2,3-double bond of the isoflavone is maintained.

2. The method of claim 1, which comprises in a second reaction step (b) attaching a protective group at the 4-position hydroxy group of the 4-hydroxy compound.

3. The method of claim 2, which comprises in a third reaction step (c) reducing the 2,3-double bond of the protected 4-hydroxy compound such that an isoflavane is obtained.

4. The method of claim 1, whereby in reaction step (a) the reduction is carried out
   enzymatically, or
   with LiAlH(O-tert-Bu).

5. The method of claim 2, wherein the protective group is selected from 2-methoxy-ethoxymethyl (MEM), benzyl, tert-butyl, toluylsulfonyl and trimethylsilyl groups.

6. The method of claim 3, whereby the reaction step (c) takes place
   by hydroboration with subsequent protolytic reaction,
   by addition of a diamide,
   by reduction with BINAP, Wilkinson-catalyst, Vaska-catalyst, or a silane, or
   enzymatically.

7. The method of claim 1, wherein the isoflavone is daidzein.

8. A method for the production of an isoflavane from an isoflavone, which method comprises the method of claim 1, wherein the isoflavane is equol.

9. A method for the production of an isoflavane from an isoflavone, which method comprises the method of claim 1, wherein the isoflavone is daidzein.

10. The method of claim 1, whereby in reaction step (a) the reduction is carried out in the presence of an organoborane.

11. The method of claim 10, wherein the organoborane is 9-BBN, Alpine borane or catecholborane.

12. The method of claim 2, which comprises attaching the protective group through etherification or esterification of the 4-position hydroxy group.

13. The method of claim 1, whereby in reaction step (a) the reduction is carried out
   in the presence of an organozinc compound, or
   by epoxidation.

* * * * *